(12) United States Patent
Burbar et al.

(10) Patent No.: US 12,310,773 B2
(45) Date of Patent: May 27, 2025

(54) PATIENT HANDLING SYSTEM COMPRISING A FIRST MOVEABLE PEDESTAL AND A SECOND MOVEABLE PEDESTAL FOR A MEDICAL IMAGING SYSTEM

(71) Applicant: Siemens Medical Solutions USA, Inc., Malvern, PA (US)

(72) Inventors: Ziad Burbar, Knoxville, TN (US); Inki Hong, Knoxville, TN (US); James L. Corbeil, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 200 days.

(21) Appl. No.: 18/004,183

(22) PCT Filed: Nov. 13, 2020

(86) PCT No.: PCT/US2020/070783
§ 371 (c)(1),
(2) Date: Jan. 4, 2023

(87) PCT Pub. No.: WO2022/103419
PCT Pub. Date: May 19, 2022

(65) Prior Publication Data
US 2023/0255573 A1 Aug. 17, 2023

(51) Int. Cl.
*A61B 6/03* (2006.01)
*A61B 6/00* (2006.01)
*A61B 6/04* (2006.01)

(52) U.S. Cl.
CPC .......... *A61B 6/4417* (2013.01); *A61B 6/035* (2013.01); *A61B 6/037* (2013.01); *A61B 6/0407* (2013.01); *A61B 6/0487* (2020.08)

(58) Field of Classification Search
CPC .......... A61B 6/03; A61B 6/032; A61B 6/035; A61B 6/037; A61B 6/04; A61B 6/0407; A61B 6/0487; A61B 6/4417
(Continued)

(56) References Cited

U.S. PATENT DOCUMENTS

| 4,034,224 A | 7/1977 | Heavens et al. |
| 5,808,468 A * | 9/1998 | Bis .......................... A61B 5/055 |
| | | 324/318 |

(Continued)

OTHER PUBLICATIONS

International Search Report for Corresponding PCT Application No. PCT/US2020/070783, dated Oct. 1, 2021.

*Primary Examiner* — Allen C. Ho (57) ABSTRACT

A patient handling system (PHS) for a medical imaging system having a tunnel that extends through at least one scanning portion of the system. The PHS includes a first moveable pedestal that supports a detachable first pallet that includes a first patient. The first pedestal moves the first pallet through the tunnel to enable scanning of the first patient. The PHS also includes a second moveable pedestal located at a tunnel exit. The second pedestal attaches to the first pallet as the first pallet moves through the tunnel and the first pedestal subsequently detaches from the first pallet. The second pedestal then moves away from the tunnel exit to remove the first pallet from the tunnel. A second patient to be scanned is simultaneously prepared for scanning on a second pallet as the first pallet is moved through the tunnel in order to increase patient throughput through system.

18 Claims, 6 Drawing Sheets

(58) Field of Classification Search
USPC .................................. 5/601; 378/20, 62, 209
See application file for complete search history.

(56) References Cited

U.S. PATENT DOCUMENTS

| | | | |
|---|---|---|---|
| 5,742,987 A | 12/1998 | Sahadevan | |
| 5,842,987 A * | 12/1998 | Sahadevan | A61B 6/04 600/407 |
| 5,851,182 A * | 12/1998 | Sahadevan | A61N 5/1049 378/65 |
| 6,269,143 B1 * | 7/2001 | Tachibana | A61N 5/1049 378/65 |
| 6,322,251 B1 * | 11/2001 | Ballhaus | A61G 13/00 378/208 |
| 6,668,403 B2 * | 12/2003 | Seufert | A61B 6/0471 5/601 |
| 6,700,949 B2 * | 3/2004 | Susami | G21K 1/04 378/19 |
| 6,754,520 B2 * | 6/2004 | DeSilets | A61B 6/032 600/407 |
| 6,955,464 B1 * | 10/2005 | Tybinkowski | A61B 6/0487 108/5 |
| 7,010,085 B2 * | 3/2006 | Kröner | A61B 6/4447 378/208 |
| 7,077,569 B1 * | 7/2006 | Tybinkowski | A61B 6/04 378/209 |
| 7,120,223 B2 * | 10/2006 | Näfstadius | A61B 6/04 5/601 |
| 7,154,096 B2 * | 12/2006 | Amano | A61B 6/037 250/363.04 |
| 7,216,383 B2 * | 5/2007 | Heinl | A61B 6/4417 5/81.1 R |
| 7,292,673 B2 * | 11/2007 | Kröner | A61B 6/4417 378/209 |
| 7,357,575 B2 * | 4/2008 | Huber | A61B 6/04 378/209 |
| 7,360,949 B2 * | 4/2008 | Izuhara | A61B 6/4405 5/601 |
| 7,397,889 B2 * | 7/2008 | Kobayashi | A61B 6/032 5/601 |
| 7,640,607 B2 * | 1/2010 | Guertin | A61B 6/4441 5/601 |
| 7,810,187 B2 * | 10/2010 | Van Es | A61B 6/0487 5/601 |
| 7,827,635 B2 * | 11/2010 | Wang | A61B 6/0407 5/601 |
| 8,172,460 B2 * | 5/2012 | Ren | A61B 6/035 5/601 |
| 8,516,636 B2 * | 8/2013 | Gagnon | A61B 5/055 5/601 |
| 8,621,689 B2 * | 1/2014 | Dong | A61B 5/055 5/601 |
| 8,692,213 B2 * | 4/2014 | Abenaim | A61B 6/0407 5/81.1 R |
| 8,731,634 B2 * | 5/2014 | Birman | A61B 6/547 600/407 |
| 8,753,009 B2 * | 6/2014 | Gregerson | A61B 6/4435 378/197 |
| 8,898,837 B2 * | 12/2014 | Iizuka | A61B 5/055 5/601 |
| 9,265,440 B2 * | 2/2016 | Menon | A61B 5/0035 |
| 9,375,187 B2 * | 6/2016 | Etters | A61B 6/0407 |
| 9,433,349 B2 * | 9/2016 | Emaci | A61B 5/704 |
| 9,737,273 B2 * | 8/2017 | Gregerson | A61B 6/4405 |
| 9,817,131 B2 * | 11/2017 | Nathan | A61B 6/4275 |
| 10,151,810 B2 * | 12/2018 | Gregerson | A61B 6/4435 |
| 10,335,096 B2 * | 7/2019 | Nett | A61G 1/02 |
| 10,595,811 B2 * | 3/2020 | Sato | A61B 6/032 |
| 10,617,368 B2 * | 4/2020 | Osaki | A61B 6/032 |
| 11,207,046 B2 * | 12/2021 | Efrati | A61B 6/037 |
| 11,257,260 B2 * | 2/2022 | Wilk | A61B 6/483 |
| 11,457,882 B2 * | 10/2022 | Shizukuishi | A61B 6/032 |
| 11,647,971 B2 * | 5/2023 | Burbar | A61B 6/037 378/206 |
| 11,653,885 B2 * | 5/2023 | Liu | A61B 6/0471 600/407 |
| 11,666,241 B2 * | 6/2023 | Shi | A61B 5/0037 600/415 |
| 11,974,866 B2 * | 5/2024 | Burbar | A61B 6/5294 |
| 12,029,691 B2 * | 7/2024 | Shizukuishi | A61B 6/0407 |
| 12,094,036 B2 * | 9/2024 | Moriyasu | A61B 6/5235 |
| 12,102,466 B2 * | 10/2024 | Bal | A61B 6/5235 |
| 12,138,096 B2 * | 11/2024 | Burbar | A61B 6/037 |
| 2013/0298328 A1 | 11/2013 | Singh | |
| 2015/0025358 A1 | 1/2015 | Emaci et al. | |

* cited by examiner

PATIENT HANDLING SYSTEM COMPRISING A FIRST MOVEABLE PEDESTAL AND A SECOND MOVEABLE PEDESTAL FOR A MEDICAL IMAGING SYSTEM

TECHNICAL FIELD

Aspects of the present invention relate to a patient handling system (PHS) for a medical imaging system having a tunnel that extends through at least one scanning portion of the imaging system, and more particularly, to a PHS that includes a first moveable pedestal that supports a detachable first pallet that moves through the tunnel to enable scanning of a first patient and a second moveable pedestal located at a tunnel exit that attaches to the first pallet as the first pallet moves through the tunnel wherein the first pedestal subsequently detaches from the first pallet and the second pedestal then moves away from the tunnel exit to remove the first pallet from the tunnel.

BACKGROUND

Positron emission tomography (PET) is a nuclear medicine imaging technique that produces a three-dimensional image or map of functional processes in a patient's body. The sensitivity performance of PET systems has been improved by improving time of flight (ToF) performance and by elongating the axial field of view (FoV) of the PET system to provide greater solid angle coverage of PET detectors. Such long axial FoV systems are expensive and thus there are cost benefits to scanning as many patients per day as possible. The improved sensitivity and ToF performances of long axial FoV systems allow the patient scan time to be reduced. However, the number of additional patients that can be scanned in a given time period is limited by the amount of time needed to prepare a patient for the scan along with loading and unloading the patient on a patient bed of the system before and after the scan.

Figure 1:
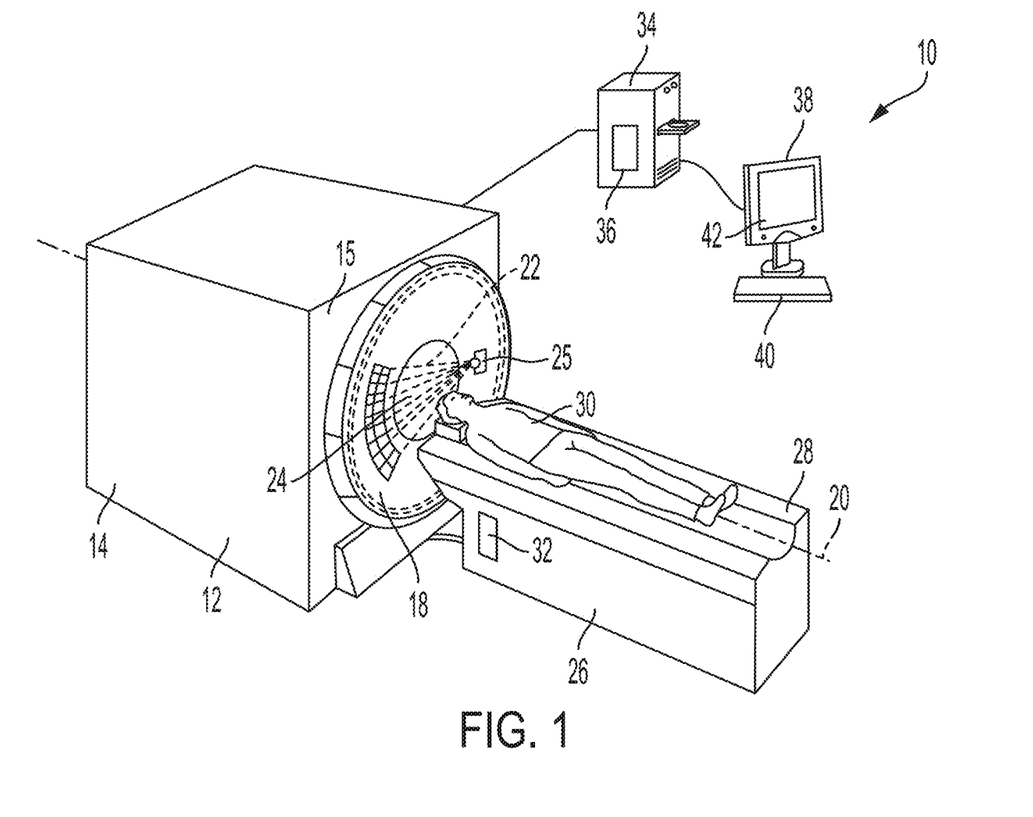
FIG. 1 depicts an exemplary PET/CT imaging system having a CT portion and a PET portion.

For example, hybrid PET/computed tomography (CT) imaging systems are frequently used to generate PET and CT images, respectively, that are co-registered to provide a combined image that gives medical personnel both anatomic and metabolic information about the patient's body. Referring to FIG. 1, an exemplary PET/CT imaging system 10 having a CT portion 12 and a PET portion 14 is shown. The CT portion 12 includes a gantry 15 having a recording unit that includes an X-ray source 25 and an X-ray detector 18. The recording unit rotates about a longitudinal axis 20 during the recording of a tomographic image, and the X-ray source 25 emits X-rays 22 during a recording.

The PET portion 14 of the system 10 includes at least one PET detector ring each including a plurality of known PET detectors arranged in a ring shape configuration on a backplane. The PET detectors define an FoV that extends in the same direction as the longitudinal axis 20. During a known operation of the PET portion of system, annihilation events occur in the FoV wherein an electron interacts with a positron to cause the generation of gamma radiation that is then detected by the PET detectors. The detection of gamma radiation is used to generate PET images which are then used in conjunction with CT images generated by the CT portion 12 of system 10 to provide images as previously described.

The system 10 includes a gantry and a tunnel 24 that extends through the CT 12 and PET 14 portions and a table base 26 having a moveable patient bed 28 that supports a patient 30. In an initial position, the bed 28 is located outside the tunnel 24 to enable loading of the patient 30. In use, the bed 28 moves from the initial position and then through the tunnel 24 to translate the patient 30 along the longitudinal axis 20 and through CT 12 and PET 14 portions in order to generate the PET and CT images, respectively. After scanning, the bed 28 then returns to the initial position to unload the patient 30. The table base 26 includes a control unit 32 connected to a computer 34 that controls operation of the system 10. The system 10 may be configured by a determination unit 36 utilizing a stored computer program that can be executed on the computer 34. The computer 34 is connected to an output device 38 such as a computer monitor and an input device 40. An output 42 on the output device 38 comprises, for example, a graphical user interface for actuating individual units of the system 10 and control unit 32. Further, different views of recorded data can be displayed on the output device 38. The input device 40 may include a keyboard and mouse, for example.

SUMMARY OF THE INVENTION

A patient handling system (PHS) for a medical imaging system is disclosed wherein the imaging system includes a tunnel that extends through at least one scanning portion of the imaging system. The PHS includes a first moveable pedestal that supports a detachable first pallet that includes a first patient. The first pedestal moves the first pallet through the tunnel to enable scanning of the first patient. The PHS also includes a second moveable pedestal located at a tunnel exit. The second pedestal attaches to the first pallet as the first pallet moves through the tunnel and the first pedestal subsequently detaches from the first pallet. The second pedestal then moves away from the tunnel exit to remove the first pallet from the tunnel. A second patient to be scanned is simultaneously prepared for scanning on a second pallet as the first pallet is moved through the tunnel in order to increase patient throughput through system.

In another embodiment, a patient handling system (PHS) for a medical imaging system is disclosed having a tunnel that extends through at least one scanning portion of the imaging system. The PHS includes a first moveable pedestal that supports a first pallet that includes a first patient wherein the first pedestal moves the first pallet through the tunnel to enable scanning of the patient. The PHS also includes a second moveable pedestal that supports a second pallet that includes a second patient wherein the first and second pallets are oriented at an angle relative to each other. Further, the PHS includes a table that rotates the imaging system to align the imaging system with either the first or second pallets wherein when the scan of the first patient is complete, the table rotates to align the imaging system with the second pallet and the second pedestal moves the second pallet through the tunnel to enable scanning of the second patient.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

DETAILED DESCRIPTION

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Figure 2A:
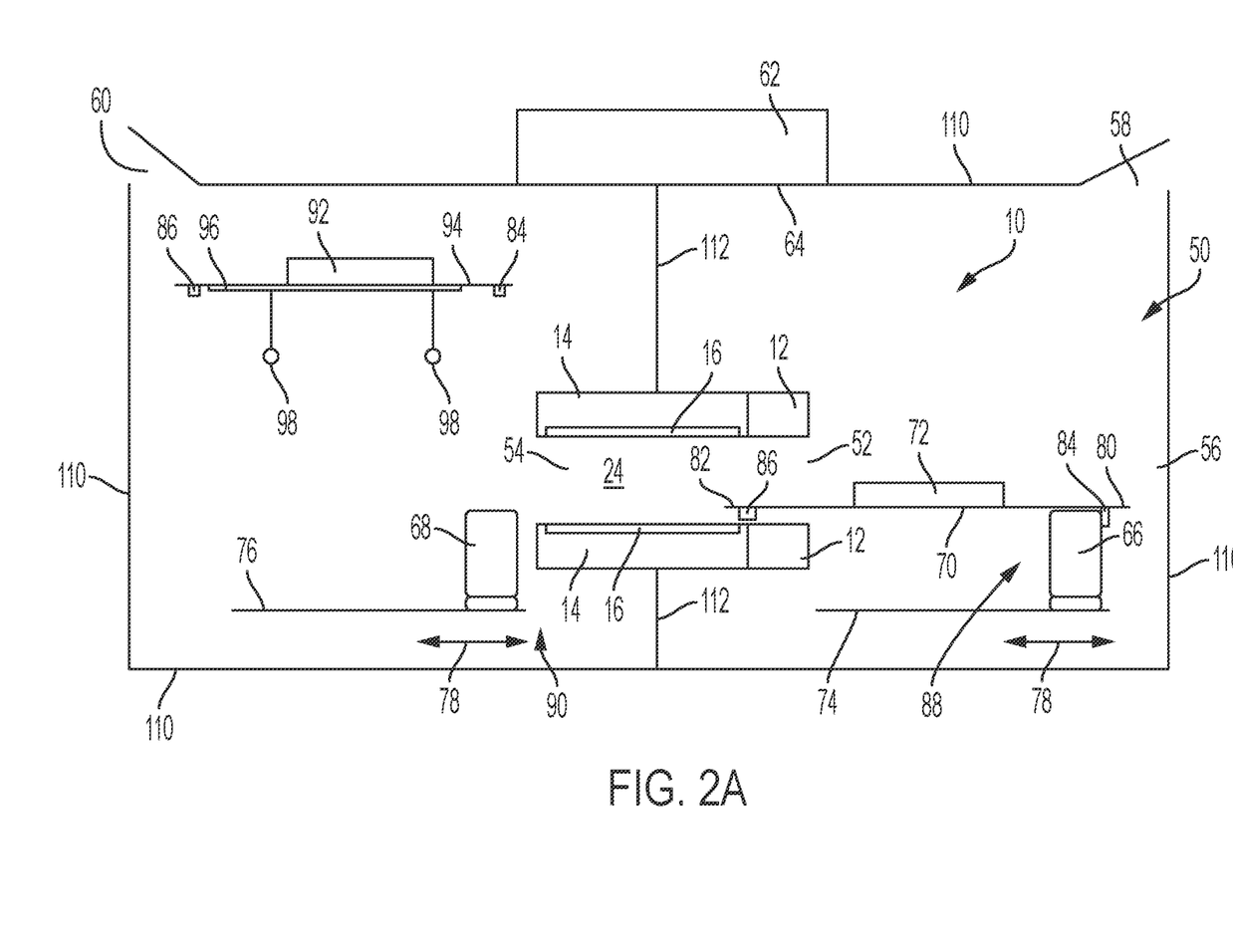
FIGS. 2A-2C depict a patient handling system (PHS) in accordance with an aspect of the invention.
Figure 2B:
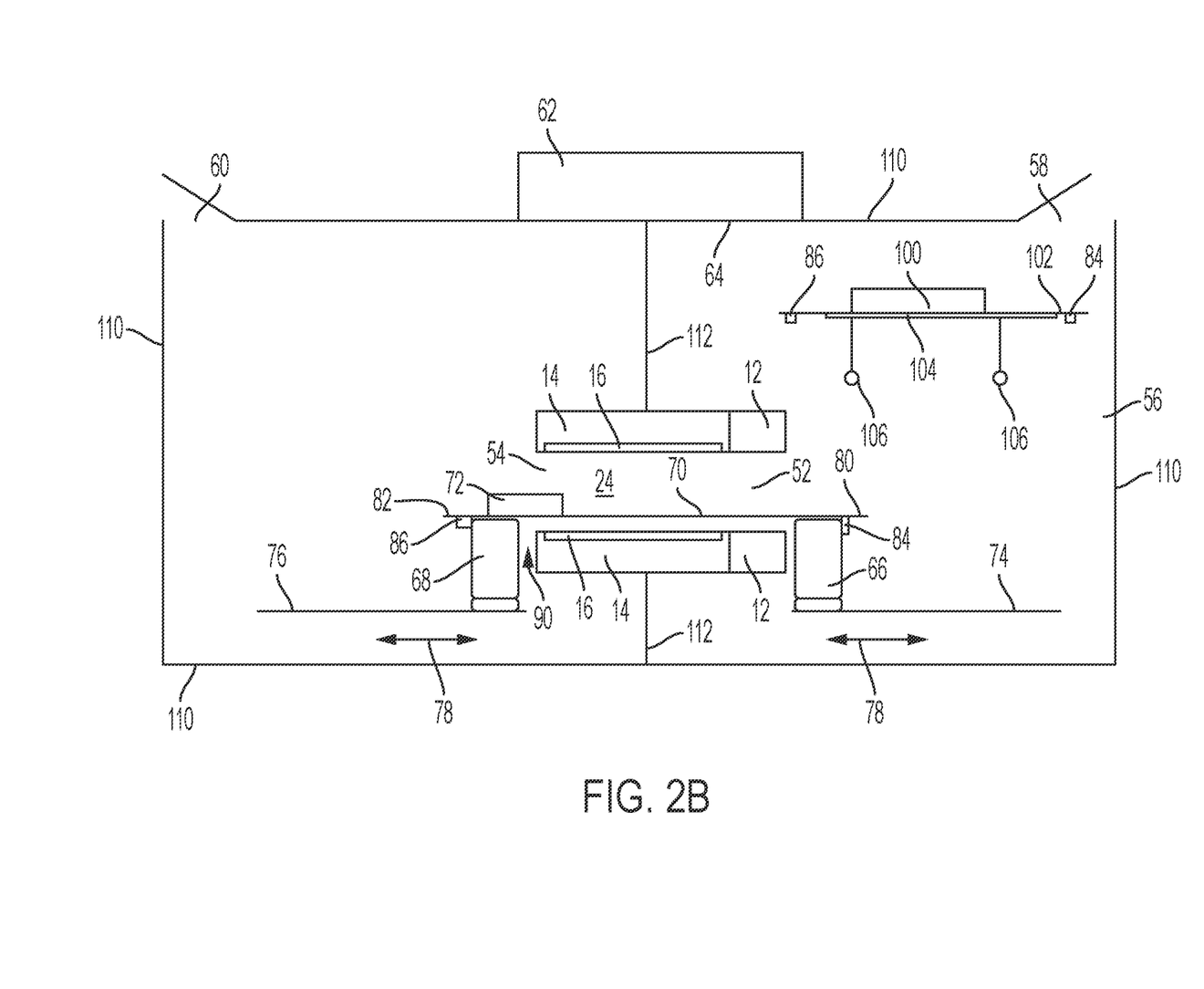
Figure 2C:
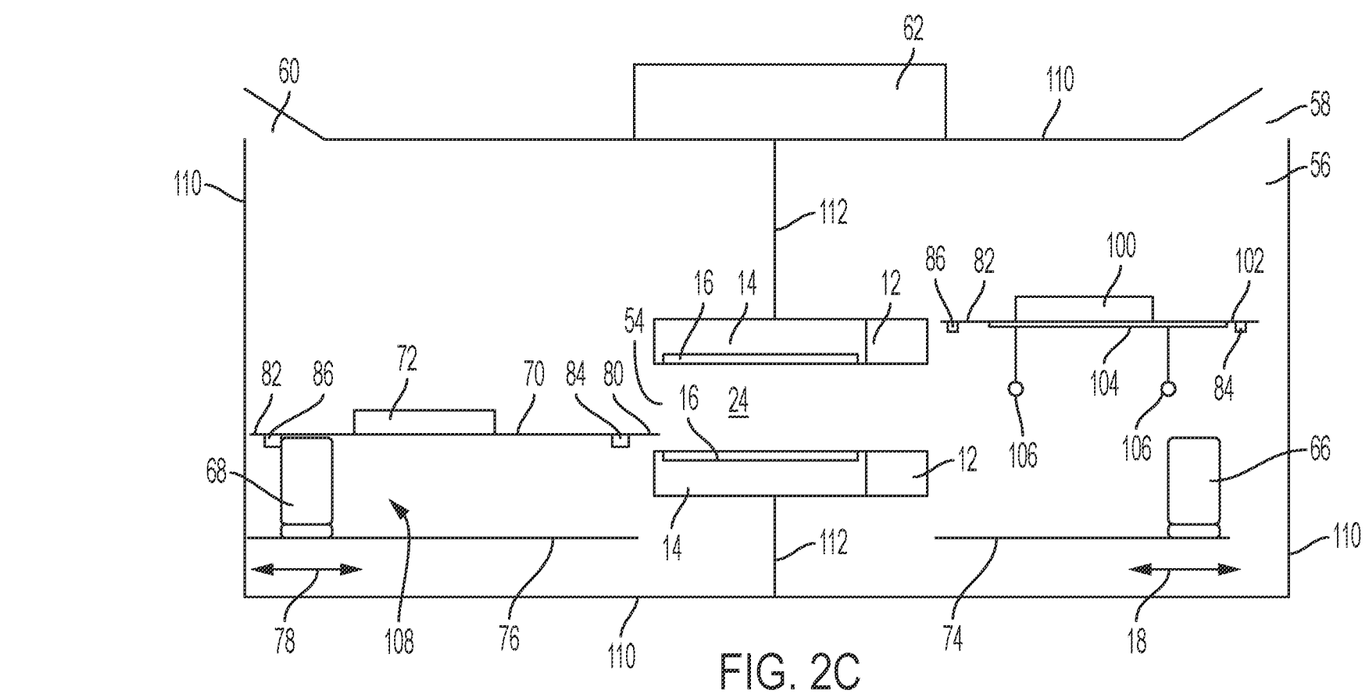

Referring to FIGS. 2A-2C, a patient handling system (PHS) 50 in accordance with an aspect of the invention is shown. The PHS 50 may be used in conjunction with a medical imaging system having a patient tunnel for receiving a patient such as a magnetic resonance imaging (MRI) system, a positron emission tomography (PET) system, a single-photon emission computed tomography (SPECT) system, a PET/MRI system, an X-ray computed tomography (CT) system, a PET/CT system, a SPECT/CT system and others. For purposes of illustration, the invention will be described in connection with the PET/CT imaging system 10 including the CT 12 and PET 14 portions having PET detectors 16. Further, the system 10 may include an elongated axial field of view that forms a long axial view system. For example, the length of a long axial field of view may be approximately 1 meter or longer. Alternatively, the invention may be used in conjunction with PET scanners having standard or shorter fields of view.

The tunnel 24 extends through the CT 12 and PET 14 portions and includes a tunnel entrance 52 and a tunnel exit 54. The PHS 50 and system 10 are shown located in a radiation shielded scan room 56 of a medical facility, for example, having an entrance 58 and exit 60 and an operator room 62 that is shielded by radiation glass 64. The PHS 50 includes first 66 and second 68 pedestals and a first patient pallet 70 that supports a first patient 72. The first 66 and second 68 pedestals are each independently moveable toward and away from the system 10. In an aspect of the invention, the first 66 and second 68 pedestals are moveably mounted to first 74 and second 76 tracks or rails, respectively, to guide movement of the first 66 and second 68 pedestals. The first 74 and second 76 tracks each include a linear actuator such as a linear motor to independently move either or both the first 66 and second 68 pedestals in a horizontal direction 78 either toward or away from the system 10. The linear motors are controlled using a motion controller in communication with a computer associated with the system 10 such as computer 34. First 80 and second 82 ends of the first pallet 70 include first 84 and second 86 attachment devices, respectively, that removably attach to the first 66 and second 68 pedestals, respectively.

In FIG. 2A, the first pedestal 66 is shown spaced apart from the tunnel entrance 52 in a loaded position 88 and the second pedestal 68 is located adjacent the tunnel exit 54 in a pallet retrieval position 90. In the loaded position 88, the first end 80 of the first pallet 70 is attached to the first pedestal 66 by the first attachment device 84 such that only the first pedestal 66 supports the first pallet 70. In addition, the first patient 72 on the first pallet 70 has been prepared for scanning by the CT 12 and PET 14 portions and is ready for scanning. The first pedestal 66 is actuated to move toward the system 10 which moves the first pallet 70 such that the second end 82 is inserted into the tunnel 24 via the tunnel entrance 52. The first pallet 70 is advanced through the tunnel 24 by the first pedestal 66 to enable successive CT and PET scans of the first patient 72 and continues advancing until the second end 82 extends from the tunnel exit 54. In FIG. 2A, a previously scanned patient 92 positioned on another pallet 94 that has been removed from the tunnel 24 and unloaded from the system 10. The pallet 94 is located on a stretcher 96 having wheels 98 to enable transport of the previously scanned patient 92 out of the room 56 via the exit 60.

Referring to FIG. 2B, the second end 82 of the first pallet 70 is shown attached to the second pedestal 68 in the pallet retrieval position 90 by the second attachment device 86. The second end 82 is attached to the second pedestal 68 when the second end 82 extends from the tunnel exit 54. The first end 80 of the first pallet 70 is then detached from the first pedestal 66 such that only the second pedestal 68 supports the first pallet 70. FIG. 2B also depicts a new or second patient 100 positioned on a second pallet 102 located on a second stretcher 104 having wheels 106 to enable transport of the second patient 100 into the room 56 via the entry 58. As the first pallet 70 is advanced through the tunnel 24 for successive CT and PET scans, the second patient 100 on the second pallet 102 is simultaneously prepared for CT and PET scanning by medical personnel. For example, preparing a patient for CT and PET scanning may include the attachment of leads from an electrocardiogram device on the patient and/or connections for respiratory devices and setup of the devices.

Referring to FIG. 2C, the second pedestal 68 moves away from the pallet retrieval position 90 to a retracted position 108 wherein the second pedestal 68 is spaced apart from the system 10 and the first pallet 70 is removed from the tunnel 24. The first pallet 70 is then detached from the second pedestal 68 to enable unloading of the first pallet 70 from the second pedestal 68. The first pallet 70 is then positioned on a stretcher 96 (as shown in FIG. 2A). As the first pallet 70 is being removed from the tunnel 24 by the second pedestal 68, the first pedestal 66 simultaneously returns to the loaded position 88 (as shown in FIG. 2A) wherein the first end 80 of the second pallet 102 is attached to the first pedestal 66 by the first attachment device 84 as previously described. When the first pallet 70 is removed from the tunnel 24, the first pedestal 66 then moves toward the system 10 such that the second end 82 of the second pallet 102 enters the tunnel 24 to enable successive CT and PET scans of the previously prepared second patient 100 and the process repeats.

Thus, patient throughput through the system 10 is optimized due to time savings which in turn reduces the total cost of ownership of the system 10. In particular, while a first patient is being scanned, a second patient is simultaneously prepared for scanning. In addition, as a first pallet including the first patient is being removed from the tunnel by the second pedestal, a second pallet including the previously prepared second patient, is simultaneously loaded on the first pedestal and is ready to be inserted into the tunnel 24 for scanning of the second patient. Further, standard production PET/CT systems and software may be used in conjunction with the PHS of the current embodiment thus minimizing costs.

The room 56 is defined by radiation shielded walls 110 and may be configured as a single long room that includes the first 66 and second 68 pedestals, pallets 70, 94, 102 stretchers 96, 104 and the system 10. Radiation shielding glass or a radiation shielded accordion room separator 112 may be used to separate the room 56. This reduces exposure of medical personnel and/or patients being prepared for scanning to X-ray radiation from another patient being scanned and/or radioactivity from a radioisotope that is injected into a patient in connection with a PET scan, for example. Alternatively, the room 56 may be separated by a wall to form adjacent rooms wherein the system 10 extends through an opening in the wall. In another configuration, two rooms and a utility room located between the two rooms may be used wherein a portion of the system 10 is located in the utility room and a remaining part of the system 10 extends through a wall of the utility room into the scan room 56.

Figure 3:
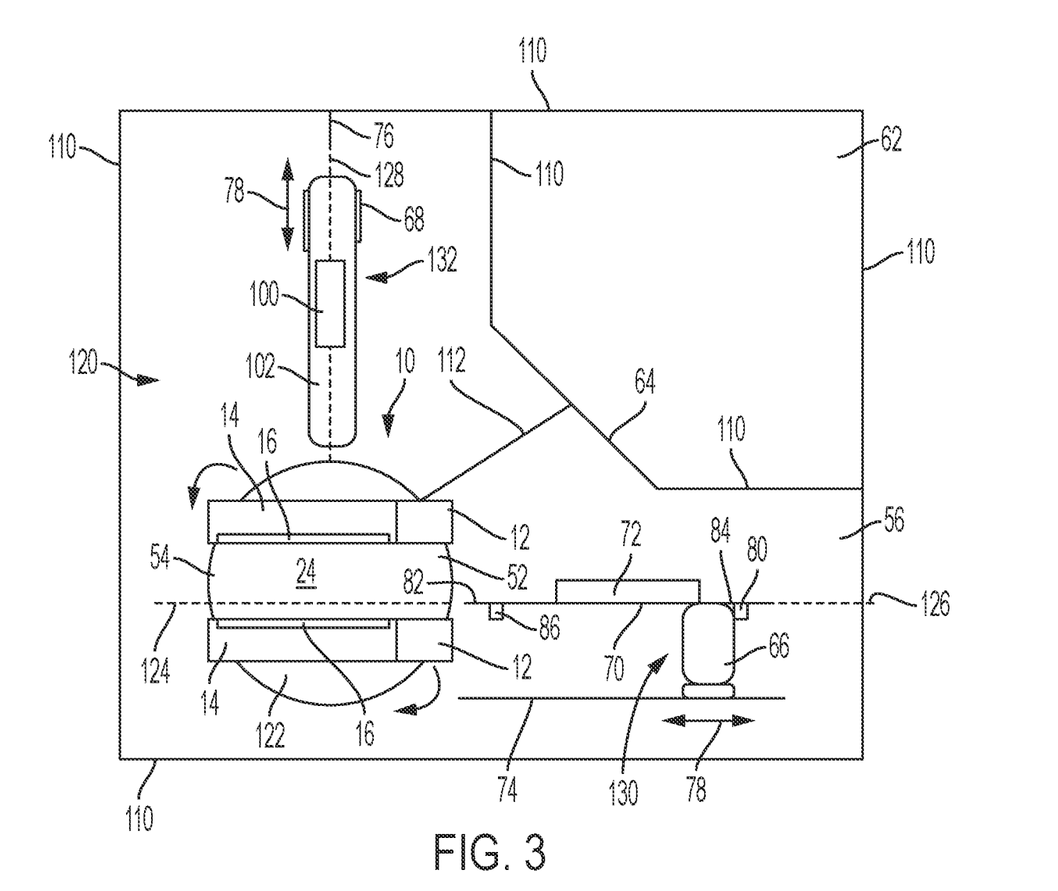
FIG. 3 depicts a PHS in accordance with an alternate embodiment of the invention.

Referring to FIG. 3, a PHS 120 in accordance with an alternate embodiment of the invention is shown. In this embodiment, the first pallet 70 is oriented at an approximately 90 degree angle relative to the second pallet 102 (shown as a top view in FIG. 3). The first 70 and second 102 pallets are attached to the first 66 and second 68 pedestals. In addition, the system 10 is located on a rotatable table 122 that enables 90 degree rotation of the system 10 to enable alignment of the system 10 with either the first 70 or second 102 pallet. It is understood that the first 70 and second 102 pallets may be oriented relative to each other at angles greater or less than 90 degrees and that the table 122 rotates in a rotation angle corresponding to the orientation of the first 70 and second 102 pallets.

The table 122 is shown oriented such that a system axis 124 is aligned with a first axis 126 of the first pallet 70 and a second axis 128 of the second pallet 102 is oriented at 90 degrees relative to the system axis 124. The first pedestal 66 is shown spaced apart from the tunnel entrance 52 in a first initial position 130 wherein a patient may be loaded or unloaded. First 72 and second 100 patients are located on the first 70 and second 102 pallets, respectively.

The first pedestal 66 is actuated to move toward the system 10 which moves the first pallet 70 such that the second end 82 is inserted into the tunnel 24 via the tunnel entrance 52. The first pallet 70 is advanced through the tunnel 24 by the first pedestal 66 to enable successive CT and PET scans of the first patient 72. As the first pallet 70 is advanced through the tunnel 24 for CT and PET scanning, the second patient 100 on the second pallet 102 is simultaneously prepared for CT and PET scanning by medical personnel. For example, preparing a patient for CT and PET scanning may include the attachment of leads from an electrocardiogram device on the patient and/or connections for respiratory devices and setup of the devices.

Once the scan of the first patient 72 is completed, the first pedestal 66 and first pallet 70 move back to the first initial position 130. The table 122 is then rotated approximately 90 degrees until the system axis 124 is aligned with the second axis 128 of the second pallet 102. In this position, the second pedestal 68 is spaced apart from the tunnel entrance 52 in a second initial position 132 in which a patient may be loaded and unloaded. The second pallet 102 is then advanced through the tunnel 24 by the second pedestal 68 to enable successive CT and PET scans of the second patient 100. As the second pallet 102 is advanced through the tunnel for CT and PET scanning, the first patient 72 is unloaded from the first pallet 70 and a third patient is loaded and simultaneously prepared for CT and PET scanning by medical personnel while on the first pallet 70. Once the scan of the second patient 100 is completed, the second pedestal 68 and second pallet 102 move back to the second initial position 132 and the process repeats as previously described. In another aspect of the invention, the first 66 and second 68 pedestals may each include a collision avoidance system in order to move either of the pedestals 66, 68 and thus the associated pallets 70, 102 toward or away from the CT portion 12 to prevent a collision between the system 10 and the pallets 70, 102. For example, the collision avoidance system may be activated if bed extensions are used.

Thus, patient throughput through the system 10 is optimized due to time savings which in turn reduces the total cost of ownership of the system. In particular, while a patient is being scanned on a first pallet 70, a previously scanned patient is unloaded from a second pallet 102 and a next patient is loaded and simultaneously prepared for scanning. Further, standard production PET/CT systems and software may be used in conjunction with the PHS 120 of the current embodiment thus minimizing costs. The room 56 may have a square or rectangular shape. In addition, the operator room 62 may be located in a corner of the room 56 such that an operator has a constant view of both sides of the system 10 so that patients and the scan room 56 may be monitored.

Figure 4:
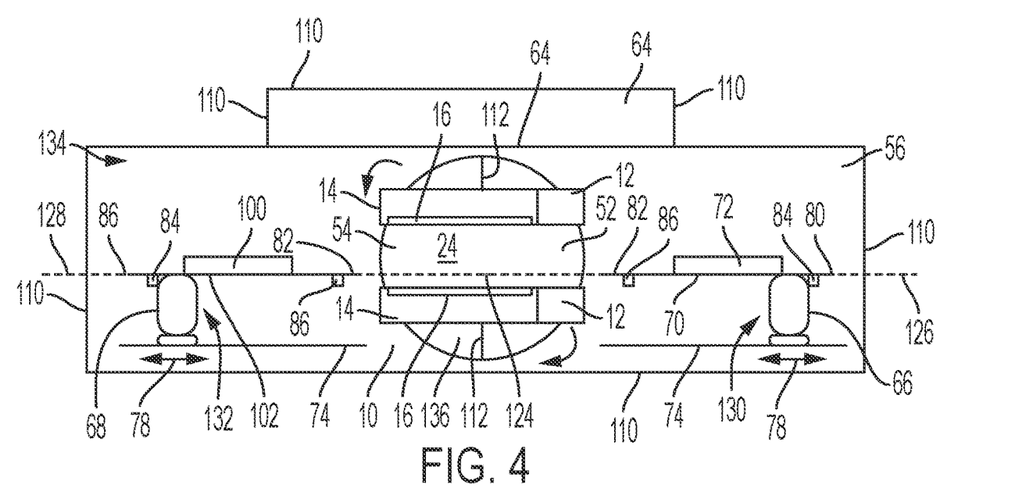
FIG. 4 depicts a PHS in accordance with a further alternate embodiment of the invention.

Referring to FIG. 4, a PHS 134 in accordance with a further alternate embodiment of the invention is shown. In this embodiment, the first pallet 70 is oriented at an approximately 180 degree angle relative to the second pallet 102. The first 70 and second 102 pallets are attached to the first 66 and second 68 pedestals, respectively, as previously described. In addition, the system 10 is located on a rotatable table 136 that enables 180 degree rotation of the system 10 to enable alignment of the system 10 with either the first 70 or second 102 pallet.

The table 136 is shown oriented such that the system axis 124 is aligned with the first 126 and second 128 axes of the first 70 and second 102 pallets, respectively. The first pedestal 66 is shown spaced apart from the tunnel entrance 52 in the first initial position 130 wherein a patient may be loaded or unloaded. First 72 and second 100 patients are located on the first 70 and second 102 pallets, respectively.

Operation of the alternate embodiment shown in FIG. 4 is similar to the embodiment shown in FIG. 3. The first pallet 70 is advanced through the tunnel 24 by the first pedestal 66 to enable successive CT and PET scans of the first patient 72. As the first pallet 70 is advanced through the tunnel 24 for CT and PET scanning, the second patient 100 on the second pallet 102 is simultaneously prepared for CT and PET scanning by medical personnel.

Once the scan of the first patient 72 is completed, the first pedestal 66 and first pallet 70 move back to the first initial position 130. The table 136 is then rotated 180 degrees until the system axis 124 is aligned with the second axis 128 of the second pallet 102. In this position, the second pedestal is spaced apart from the tunnel entrance 52 in the second initial position 132 wherein a patient may be loaded and unloaded.

The second pallet 102 is then advanced through the tunnel 24 by the second pedestal 66 to enable successive CT and PET scans of the second patient 100. As the second pallet 102 is advanced through the tunnel 24 for CT and PET scanning, the first patient 72 is unloaded from the first pallet 70 and a third patient is loaded and simultaneously prepared for CT and PET scanning by medical personnel while on the first pallet 70. Once the scan of the second patient 100 is completed, the second pedestal 68 and second pallet 102 move back to the second initial position 132 and the process repeats as previously described.

Figure 5:
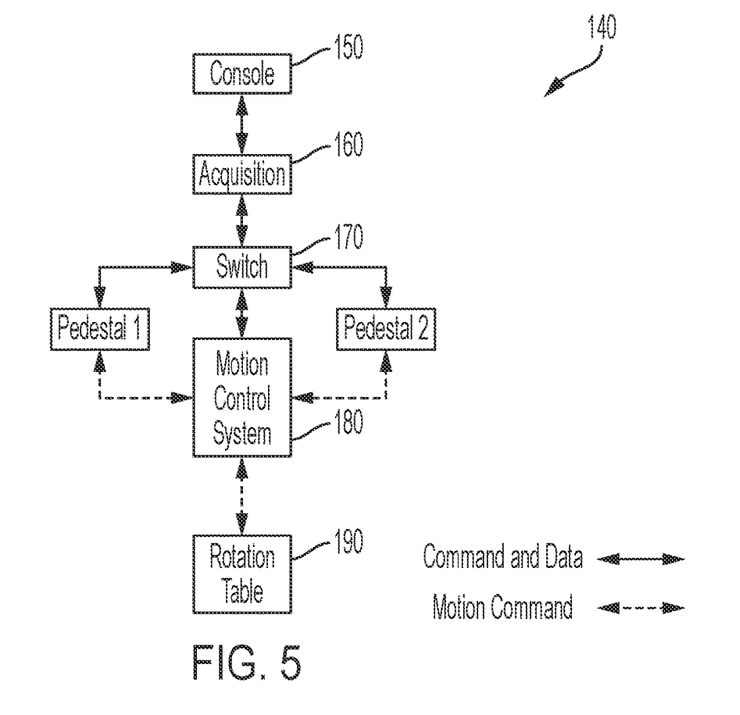
FIG. 5 shows a flowchart for an acquisition and motion control system for the alternate embodiments shown in FIGS. 3 and 4.

FIG. 5 shows a flowchart 140 for an acquisition and motion control system for the embodiments shown in FIGS. 3 and 4. A console computer is the interface between the system and the operator and includes a display or multiple displays that display the status of each scan. The operator enters patient information, scan protocol, dosage, the pedestal used to scan the patient and other information into the computer at Step 150. The scan protocol is then passed to an acquisition system that manages data acquisition from the system as Step 160. A pedestal used to scan the patient is switched at Step 170. A selected pedestal is controlled at Step 180 by a motion control system. In addition, table rotation is controlled at Step 190 by the motion control system.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A patient handling system (PHS) for a medical imaging system having a tunnel that extends through at least one scanning portion of the medical imaging system, comprising:
   a first moveable pedestal comprising a detachable first pallet that includes a first patient, wherein the first moveable pedestal moves the detachable first pallet through the tunnel to enable scanning of the first patient; and
   a second moveable pedestal located at a tunnel exit, wherein the second moveable pedestal attaches to the detachable first pallet as the detachable first pallet moves through the tunnel, and the first moveable pedestal subsequently detaches from the detachable first pallet, and wherein the second moveable pedestal moves away from the tunnel exit to remove the detachable first pallet from the tunnel.

2. The PHS according to claim 1, further comprising a second pallet including a second patient prepared for scanning is attached to the first moveable pedestal simultaneously with the second moveable pedestal removing the detachable first pallet from the tunnel in order to increase a patient throughput through the medical imaging system.

3. The PHS according to claim 2, wherein the second patient is simultaneously prepared for scanning on the second pallet as the detachable first pallet is moved through the tunnel during scanning in order to increase a patient throughput through the medical imaging system.

4. The PHS according to claim 2, wherein the first moveable pedestal is spaced apart from the tunnel in a loaded position when the second pallet is attached to the first moveable pedestal.

5. The PHS according to claim 1, wherein a first end and a second end of the detachable first pallet are removably attached to the first moveable pedestal and the second moveable pedestal, respectively.

6. The PHS according to claim 1, wherein the second moveable pedestal moves to a retracted position when the detachable first pallet is removed from the tunnel, wherein the second moveable pedestal is spaced apart from the tunnel exit in the retracted position.

7. The PHS according to claim 1, further comprising a first track and a second track, wherein the first moveable pedestal and the second moveable pedestal are moveably mounted to the first track and the second track, respectively, that guide a movement of the first moveable pedestal and the second moveable pedestal.

8. A patient handling system (PHS) for a positron emission tomography/computed tomography (PET/CT) medical imaging system having a PET portion, a CT portion, and a tunnel that extends through at least one of the PET portion and the CT portion of the PET/CT medical imaging system, comprising:
   a first moveable pedestal comprising a detachable first pallet that includes a first patient, wherein the first moveable pedestal moves the detachable first pallet through the tunnel, the PET portion, and the CT portion of the PET/CT medical imaging system to enable scanning of the first patient; and
   a second moveable pedestal located at a tunnel exit, wherein the second moveable pedestal attaches to the detachable first pallet as the detachable first pallet moves through the tunnel, and the first moveable pedestal subsequently detaches from the detachable first pallet, and wherein the second moveable pedestal moves away from the tunnel exit to remove the detachable first pallet from the tunnel.

9. The PHS according to claim 8, wherein the PET portion of the PET/CT imaging system has a long axial field of view.

10. A patient handling system (PHS) for a medical imaging system having a tunnel that extends through at least one scanning portion of the medical imaging system, comprising:
    a first moveable pedestal comprising a first pallet that includes a first patient, wherein the first moveable pedestal moves the first pallet through the tunnel to enable scanning of the first patient;
    a second moveable pedestal comprising a second pallet that includes a second patient, wherein the first pallet and the second pallet are oriented at an angle relative to each other; and
    a table that rotates the medical imaging system to align the medical imaging system with either the first pallet or the second pallet, wherein when a scan of the first patient is complete, the table rotates to align the medical imaging system with the second pallet, and the second moveable pedestal moves the second pallet through the tunnel to enable scanning of the second patient.

11. The PHS according to claim 10, wherein the first moveable pedestal and the first pallet move to a first initial position after scanning, wherein the first moveable pedestal is spaced apart from a tunnel entrance to enable loading or unloading of a next patient.

12. The PHS according to claim 10, wherein the first moveable pedestal and the second moveable pedestal are oriented at an angle of either 90 degrees or 180 degrees relative to each other.

13. A patient handling system (PHS) for a positron emission tomography/computed tomography (PET/CT) medical imaging system having a PET portion, a CT portion, and a tunnel that extends through at least one of the PET portion and the CT portion of the (PET/CT) medical imaging system, comprising:
- a first moveable pedestal comprising a first pallet that includes a first patient, wherein the first moveable pedestal moves the first pallet through the tunnel, the PET portion, and the CT portion of the PET/CT medical imaging system to enable scanning of the first patient;
- a second moveable pedestal comprising a second pallet that includes a second patient, wherein the first pallet and the second pallet are oriented at an angle relative to each other; and
- a table that rotates the PET/CT medical imaging system to align the PET/CT medical imaging system with either the first pallet or the second pallet, wherein when a scan of the first patient is complete, the table rotates to align the PET/CT medical imaging system with the second pallet, and the second moveable pedestal moves the second pallet through the tunnel to enable scanning of the second patient.

14. The PHS according to claim 13, wherein the PET portion of the PET/CT imaging system has a long axial field of view.

15. A method of increasing a patient throughput of a medical imaging system having a tunnel that extends through at least one scanning portion of the medical imaging system, comprising:
- providing a first moveable pedestal comprising a detachable first pallet that includes a first patient, wherein the first moveable pedestal moves the detachable first pallet through the tunnel to enable scanning of the first patient;
- providing a second moveable pedestal comprising a second pallet located at a tunnel exit, wherein the second moveable pedestal attaches to the detachable first pallet as the detachable first pallet moves through the tunnel, and the first moveable pedestal subsequently detaches from the detachable first pallet, and wherein the second moveable pedestal moves away from the tunnel exit to remove the detachable first pallet from the tunnel; and
- simultaneously preparing a second patient on the second pallet for scanning on the second pallet as the detachable first pallet is moved through the tunnel during scanning.

16. The method according to claim 15, further including removably attaching a first end and a second end of the detachable first pallet to the first moveable pedestal and the second moveable pedestal, respectively.

17. The method according to claim 15, wherein the medical imaging system comprises a positron emission tomography (PET)/computed tomography (CT) imaging system having a long axial field of view.

18. The method according to claim 15, wherein the second patient is prepared for scanning by attaching leads of a medical device on the second patient, or connecting and setting up medical devices.

* * * * *